US008710841B2

(12) United States Patent
Stubbs et al.

(10) Patent No.: US 8,710,841 B2
(45) Date of Patent: Apr. 29, 2014

(54) SENSING DURING MAGNETIC RESONANCE IMAGING

(75) Inventors: Scott R. Stubbs, Maple Grove, MN (US); Yingbo Li, Woodbury, MN (US); Joseph M. Bocek, Seattle, WA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 525 days.

(21) Appl. No.: 12/966,526

(22) Filed: Dec. 13, 2010

(65) Prior Publication Data

US 2011/0156706 A1 Jun. 30, 2011

Related U.S. Application Data

(60) Provisional application No. 61/291,309, filed on Dec. 30, 2009.

(51) Int. Cl.
*G01V 3/00* (2006.01)

(52) U.S. Cl.
USPC .......................................... 324/318

(58) Field of Classification Search
USPC .................................. 324/300–322
See application file for complete search history.

(56) References Cited

U.S. PATENT DOCUMENTS

| 2005/0070786 | A1 | 3/2005 | Zeijlemaker et al. | |
|---|---|---|---|---|
| 2006/0293591 | A1* | 12/2006 | Wahlstrand et al. | 600/423 |
| 2008/0154342 | A1* | 6/2008 | Digby et al. | 607/63 |
| 2009/0138058 | A1* | 5/2009 | Cooke et al. | 607/5 |

FOREIGN PATENT DOCUMENTS

| WO | WO-2006/124481 A2 | 11/2006 |
|---|---|---|
| WO | WO-2011/090594 A1 | 7/2011 |

OTHER PUBLICATIONS

"International Application Serial No. PCT/US2010/060070, International Preliminary Report on Patentability mailed Jul. 12, 2012", 8 pgs.
"International Application Serial No. PCT/US2010/060070, International Search Report mailed May 27, 2011", 3 pgs.
"International Application Serial No. PCT/US2010/060070, Written Opinion mailed May 27, 2011", 7 pgs.

* cited by examiner

*Primary Examiner* — Melissa Koval
*Assistant Examiner* — Daniel Miller
(74) *Attorney, Agent, or Firm* — Schwegman Lundberg & Woessner, P.A.

(57) ABSTRACT

Physiologic information can be received from a subject during a portion of a magnetic resonance imaging (MRI) session using a sensing circuit of an implantable medical device (IMD). An indication of an active MRI scan can be received, and a time period to inhibit use of physiological information from the subject can be determined following the received indication of the active MRI scan.

18 Claims, 4 Drawing Sheets

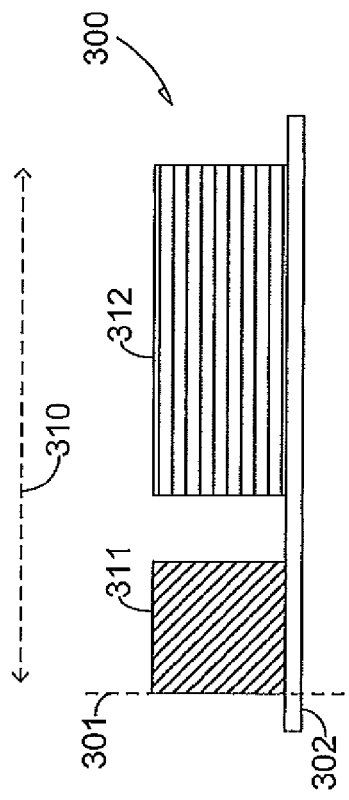
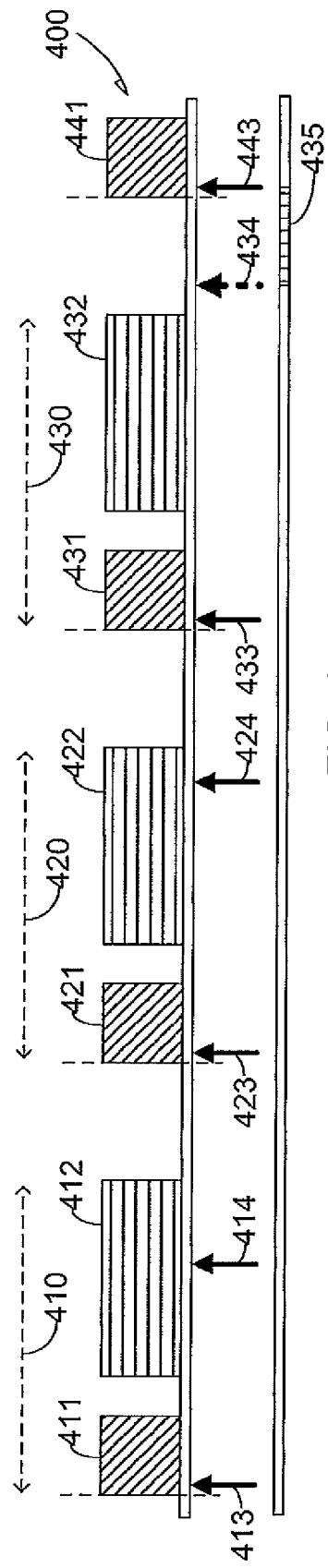

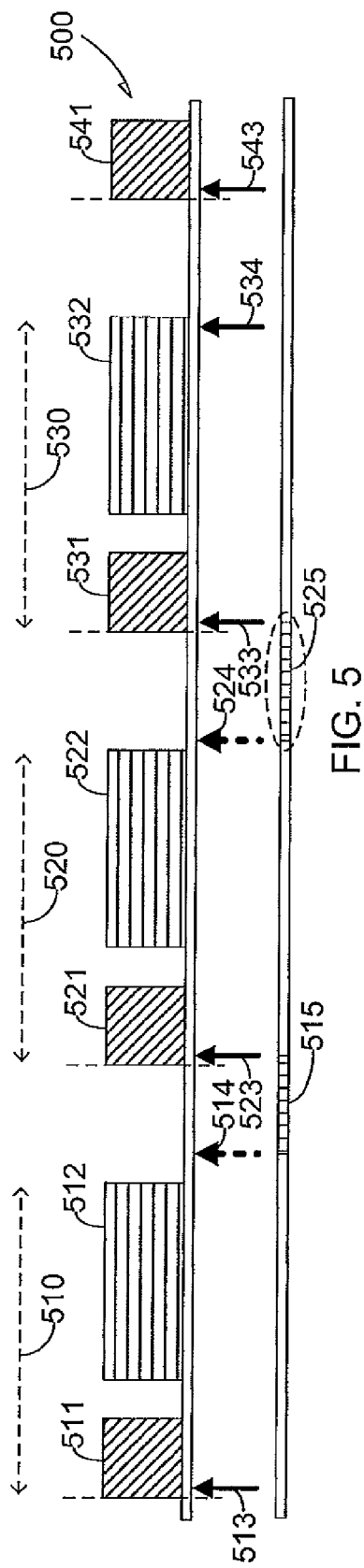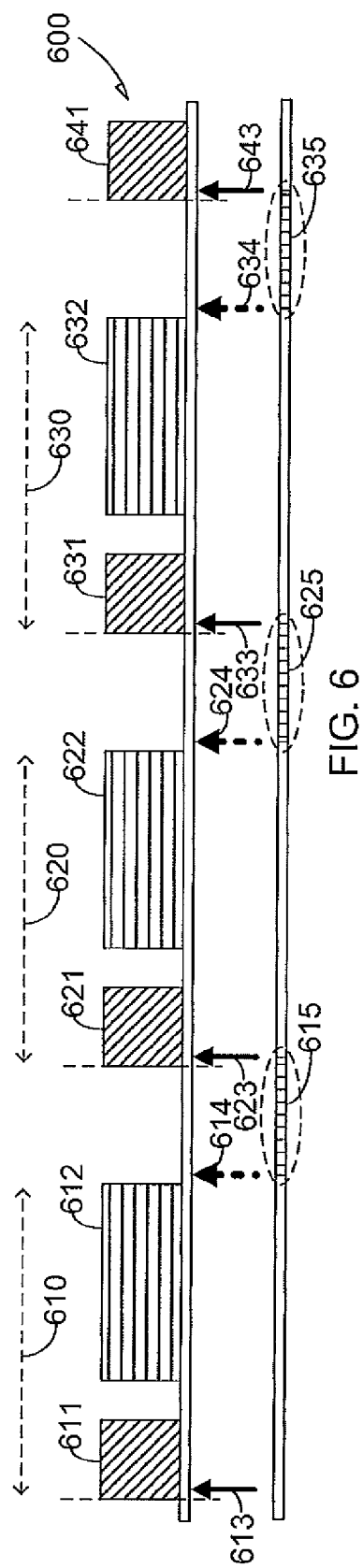

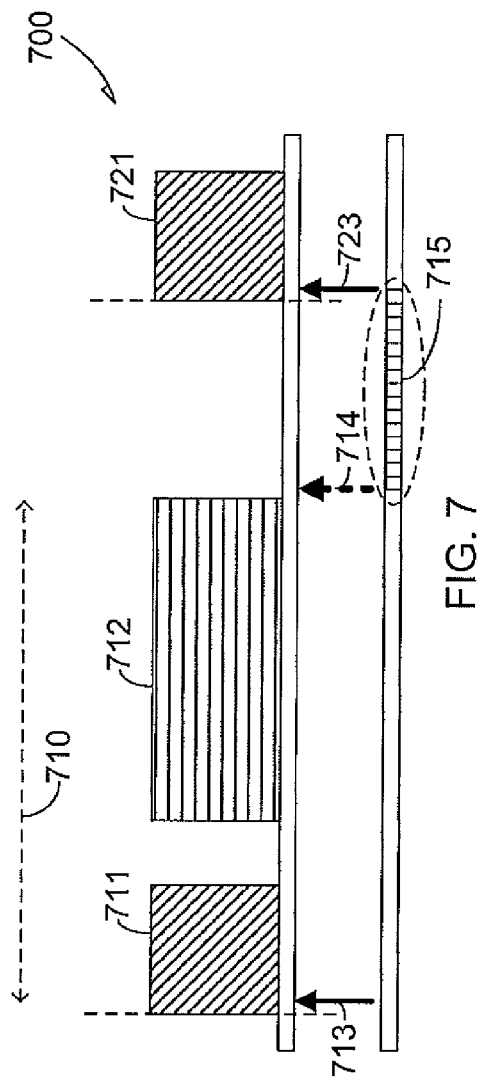
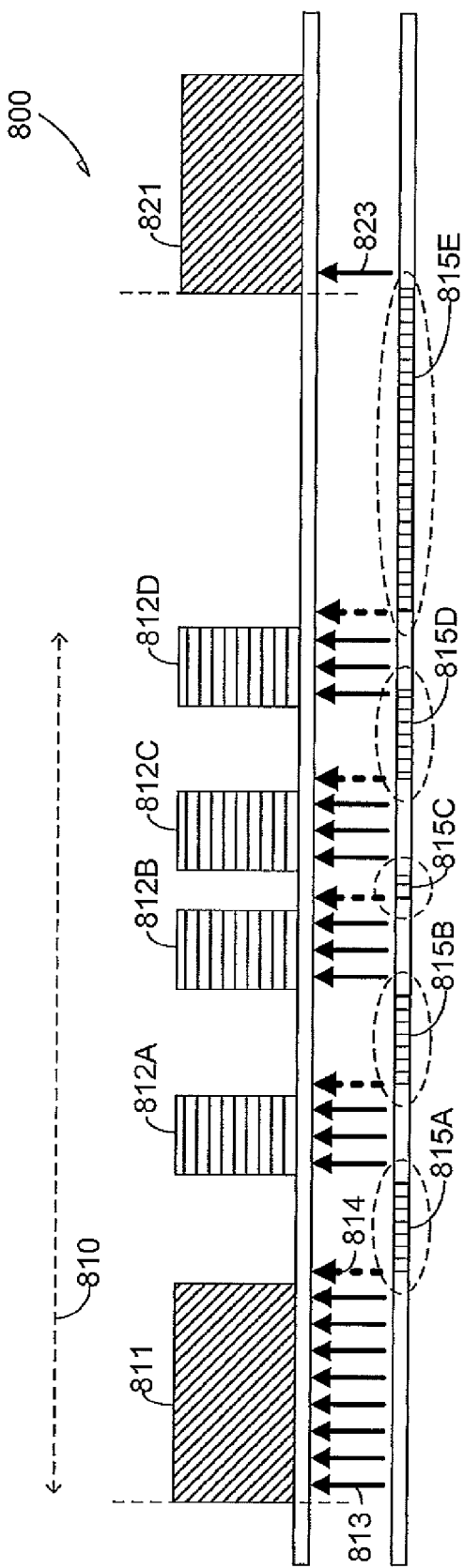

US 8,710,841 B2

SENSING DURING MAGNETIC RESONANCE IMAGING

CLAIM OF PRIORITY

This application claims the benefit of priority under 35 U.S.C. §119(e) to Stubbs et al. U.S. Provisional Patent Application Ser. No. 61/291,309, entitled "SENSING DURING MAGNETIC RESONANCE IMAGING," filed on Dec. 30, 2009, which is hereby incorporated by reference herein in its entirety.

BACKGROUND

Implantable medical devices (IMDs) can perform a variety of diagnostic or therapeutic functions. For example, an IMD can include one or more cardiac function management features, such as to monitor or to provide electrical stimulation to a heart or to the nervous system, such as to diagnose or treat a subject, such as one or more electrical or mechanical abnormalities of the heart. Examples of IMDs can include pacers, automatic implantable cardioverter-defibrillators (ICDs), or cardiac resynchronization therapy (CRT) devices, among others. Nuclear magnetic resonance imaging (MRI) is a medical imaging technique that can be used to visualize internal structure of the body. MRI is an increasingly common diagnostic tool, but can pose risks to a person with an IMD, such as a patient undergoing an MRI scan or a person nearby MRI equipment, or to people having a conductive implant.

OVERVIEW

Physiologic information can be received from a subject during a portion of a magnetic resonance imaging (MRI) session using a sensing circuit of an implantable medical device (IMD). An indication of an active MRI scan can be received, and a time period to inhibit use of physiological information from the subject can be determined following the received indication of the active MRI scan.

In Example 1, a system includes an implantable medical device (IMD) configured to be implanted into a subject, the IMD including a sensing circuit configured to receive physiologic information from the subject during a portion of a magnetic resonance imaging (MRI) session, wherein the IMD is configured to receive an indication of an active MRI scan and to determine a time period to inhibit use of physiologic information from the subject following the received indication of the active MRI scan.

In Example 2, the IMD of Example 1 is optionally configured to inhibit use of the received physiologic information from the subject for an initial time period following the received indication of the active MRI scan, to optionally receive an indication of an active MRI scan following the initial time period, and to optionally adjust the initial time period to determine an optimal time period using the indication of the active MRI scan following the initial time period.

In Example 3, the IMD of any one or more of Examples 1-2 is optionally configured to increase the initial time period until an indication of the active MRI scan is not received.

In Example 4, the IMD of any one or more of Examples 1-3 is optionally configured to decrease the initial time period until an indication of the active MRI scan is received.

In Example 5, the IMD of any one or more of Examples 1-4 is optionally configured to increase the initial time period until an indication of the active MRI scan is not received at the end of the initial time period, and then to decrease the initial time period until an indication of the active MRI scan is received at the end of the initial time period.

In Example 6, the IMD of any one or more of Examples 1-5 is optionally configured to determine an optimal time period, the optimal time period including the last decreasing initial time period prior to the indication of the active MRI scan being received at the end of the initial time period.

In Example 7, the IMD of any one or more of Examples 1-6 is optionally configured to provide a therapy to the subject, to receive an indication of proximity to a magnetic field, and to alter at least one therapy parameter in response to the received indication of proximity to the magnetic field.

In Example 8, any one or more of Examples 1-7 optionally includes a static magnetic field sensor configured to detect a static magnetic field, and the IMD of any one or more of Examples 1-7 is optionally configured to receive the indication of proximity to the magnetic field using the detected static magnetic field.

In Example 9, the IMD of any one or more of Examples 1-8 is optionally configured to receive an indication of an active MRI scan including at least one of a time-varying gradient magnetic field or an RF magnetic excitation pulse, a user indication of an active MRI scan, or information from an MRI scanner indicative of an active MRI scan.

In Example 10, any one or more of Examples 1-9 optionally includes an active magnetic field sensor configured to detect at least one of a time-varying gradient magnetic field or an RF magnetic excitation pulse of an active MRI scan, wherein the IMD of any one or more of Examples 1-9 is optionally configured to receive the indication of the active MRI scan using the active magnetic field sensor.

In Example 11, any one or more of Examples 1-10 optionally includes an implantable medical device (IMD) configured to be implanted into a subject, the IMD optionally including a sensing circuit configured to receive physiologic information from the subject during a portion of a magnetic resonance imaging (MRI) session, wherein the IMD is optionally configured to receive an indication of an active MRI scan, to inhibit use of physiologic information from the subject for an initial time period following the received indication of the active MRI scan, and to receive an indication of an active MRI scan following the initial time period, the active MRI scan optionally including at least one of a time-varying gradient magnetic field or an RF magnetic excitation pulse, wherein the IMD is optionally configured to adjust the initial time period to determine an optimal time period using the indication of the active MRI scan following the initial time period.

In Example 12, the IMD of any one or more of Examples 1-11 is optionally configured to increase the initial time period until an indication of the active MRI scan is not received at the end of the initial time period and then decrease the initial time period until an indication of the active MRI scan is received at the end of the initial time period to determine the optimal time period, wherein the optimal time period of any one or more of Examples 1-11 optionally includes the last decreasing initial time period prior to the indication of the active MRI scan being received at the end of the initial time period.

In Example 13, any one or more of Examples 1-12 optionally includes receiving physiologic information from a subject during a portion of a magnetic resonance imaging (MRI) session using a sensing circuit of an implantable medical device (IMD), receiving an indication of an active MRI scan, and determining a time period to inhibit use of the physiologic information from the subject following the received indication of the active MRI scan.

In Example 14, the determining the time period of any one or more of Examples 1-13 optionally includes inhibiting use of the received physiologic information from the subject for an initial time period following the received indication of the active MRI scan, receiving an indication of an active MRI scan following the initial time period, and adjusting the initial time period to determine an optimal time period using the indication of the active MRI scan following the initial time period.

In Example 15, the adjusting the initial time period of any one or more of Examples 1-14 optionally includes increasing the initial time period until an indication of the active MRI scan is not received.

In Example 16, the adjusting the initial time period of any one or more of Examples 1-15 optionally includes decreasing the initial time period until an indication of the active MRI scan is received.

In Example 17, the adjusting the initial time period of any one or more of Examples 1-16 optionally includes increasing the initial time period at a first rate until an indication of the active MRI scan is not received at the end of the increasing initial time period, and then decreasing the initial time period at a second rate until an indication of the active MRI scan is received at the end of the decreasing initial time period, wherein the second rate is larger in magnitude than the first rate.

In Example 18, any one or more of Examples 1-17 optionally includes determining an optimal time period includes selecting the last decreasing initial time period prior to the indication of the active MRI scan being received at the end of the initial time period.

In Example 19, any one or more of Examples 1-18 optionally includes receiving at least one of an indication of the active MRI scan including at least one of a time-varying gradient magnetic field or an RF magnetic excitation pulse, a user indication of an active MRI scan, or information from an MRI scan, or information from an MRI scanner indicative of an active MRI scan.

In Example 20, any one or more of Examples 1-19 optionally includes detecting at least one of a time-varying gradient magnetic field or an RF magnetic excitation pulse of an active MRI scan using an active magnetic field sensor, wherein the receiving the indication of the active MRI scan optionally includes receiving information from the active magnetic field sensor.

In Example 21, a system or apparatus can include, or can optionally be combined with any portion or combination of any portions of any one or more of Examples 1-20 to include, means for performing any one or more of the functions of Examples 1-20, or a machine-readable medium including instructions that, when performed by a machine, cause the machine to perform any one or more of the functions of Examples 1-20.

The examples provided herein can be combined in any permutation or combination. This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 3 illustrates generally an example of a first MRI scan portion of an MRI scan session including first initial scan slice RF and gradient pulses and first variable RF/gradient pulses.

FIG. 4 illustrates generally an example of first, second, and third scan portions of an MRI scan session, including first, second, and third initial pulses and first, second, and third variable pulses.

FIG. 5 illustrates generally an example of first, second, and third scan portions of an MRI scan session, including first, second, and third initial pulses and first, second, and third variable pulses.

FIG. 6 illustrates generally an example of first, second, and third scan portions of an MRI scan session, including first, second, and third initial pulses and first, second, and third variable pulses.

FIG. 7 illustrates generally an example of a first scan portion including a first initial pulse and a first variable pulse.

FIG. 8 illustrates generally an example including a more detailed first scan portion, including a first initial pulse and a separate first, second, third, and fourth variable pulse portions.

DETAILED DESCRIPTION

Figure 1:
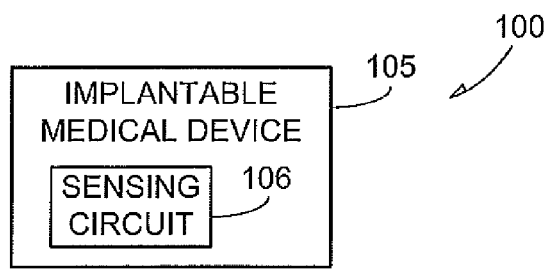
FIG. 1 illustrates generally an example of a system including an IMD configured to be implanted in a subject.

Nuclear magnetic resonance (NMR) devices (e.g., an MRI scanner, an NMR spectrometer, or other NMR device) can produce both static and time-varying magnetic fields. For example, an MRI scanner can provide a strong static magnetic field, $B_0$, such as to align nuclei within a subject to the axis of the $B_0$ field. The $B_0$ can provide a slight net magnetization (e.g., a "spin polarization") among the nuclei in bulk because the spin states of the nuclei are not randomly distributed among the possible spin states. Because the resolution attainable by NMR devices can be related to the magnitude of the $B_0$ field, a stronger $B_0$ field can be used to spin polarize the subject's nuclei to obtain finer resolution images. NMR devices can be classified according the magnitude of the $B_0$ field used during imaging, such as a 1.5 Tesla $B_0$ field, a 3.0 Tesla $B_0$ field, etc.

After nuclei are aligned using the $B_0$ field, one or more radio frequency (RF) magnetic excitation pulses can be delivered such as to alter the alignment of specified nuclei (e.g., within a particular volume or plane to be imaged within the subject). The power, phase, and range of frequencies of the one or more RF excitation pulses can be selected, such as depending on the magnitude of the $B_0$ field, the type or resonant frequency of the nuclei to be imaged, or one or more other factors. After the RF excitation pulses are turned off, one or more RF receivers can be used to detect a time-varying magnetic field (e.g., a flux) developed by the nuclei as they relax back to a lower energy state, such as the spin polarized state induced by the static magnetic field, $B_0$.

One or more gradient magnetic fields can also be provided during magnetic resonance (MR), such as to create a slight position-dependent variation in the static polarization field. The variation in the static polarization field slightly alters the resonant frequency of the relaxing nuclei, such as during relaxation after excitation by the one or more RF pulses. Using the gradient field along with the static field can provide "spatial localization" of signals detected by the RF receiver, such as by using frequency discrimination. Using a gradient field can allow a volume or a plane to be imaged more efficiently. In a gradient field example, signals received from relaxing nuclei can include energy in respective unique frequency ranges corresponding to the respective locations of the nuclei.

Active MRI equipment can induce unwanted torques, forces, or heating in an IMD or other conductive implant, or can interfere with operation of the IMD. In certain examples, the interference can include disruption in sensing by the IMD, interference in communication between the IMD and other implants or external modules during MRI operation, or disruption in monitoring or therapeutic function of the IMD.

During an MRI scan, the one or more RF excitation pulses can include energy delivered at frequencies from less than 10 MHz to more than 100 MHz, such as corresponding to the nuclear magnetic resonances of the subject nuclei to be imaged. The gradient magnetic field can include energy delivered at frequencies lower than the RF excitation pulses, because most of the AC energy included in the gradient field is provided when the gradient field is ramping or "slewing." The one or more gradient magnetic fields can be provided in multiple axes, such as including individual time-varying gradient fields provided in each of the axes to provide imaging in multiple dimensions.

In an example, the static field, $B_0$, can induce unwanted forces or torques on ferromagnetic materials, such as steel or nickel. The forces or torques can occur even when the materials are not directly within the "bore" of the MRI equipment, because significant fields can exist near the MRI equipment. Moreover, if an electric current is switched on or off in the presence of the $B_0$ field, a significant torque or force can be suddenly imposed in the plane of the circulation of the current, even though the $B_0$ field itself is static. The induced force or torque can be minimal for small currents, but the torque can be significant for larger currents, such as those delivered during shock therapy. For example, assuming the circulating current is circulating in a plane normal (e.g., perpendicular) to the static field, the torque can be proportional to the magnitude of the $B_0$ field, multiplied by the surface area of the current loop, multiplied by the current.

Time-varying fields, such as the gradient field or the field associated with the RF excitation pulse, can present different risks than the static field, $B_0$. For example, the behavior of a wire loop in the presence of a time-varying magnetic field can be described using Faraday's law, which can be represented by $$\varepsilon = -\frac{d\Phi_{B_1}}{dt},$$

in which $\varepsilon$ can represent the electromotive force (e.g., in volts), such as developed by a time-varying magnetic flux. The magnetic flux can be represent as $$\Phi_{B_1} = \int_S \int B_1 \cdot dS,$$

in which $B_1$ can represent an instantaneous magnetic flux density vector (e.g., in Webers per square meter, or Tesla). If $B_1$ is relatively uniform over the surface S, then the magnetic flux can be approximately $\Phi_{B_1}=|B_1||A|$, where A can represent the area of the surface S. Operating MRI equipment can produce a time-varying gradient field having a slew rates in excess of 100 Tesla per second (T/s). The slew rate can be similar to a "slope" of the gradient field, and is thus similar to $$\frac{d\Phi_{B_1}}{dt}.$$

The electromotive force (EMF) of Faraday's law can cause an unwanted heating effect in a conductor, regardless of whether the conductor is ferromagnetic. EMF can induce current flow in a conductor (e.g., a housing of an IMD, one or more other conductive regions within an IMD, or one or more other conductive implants). The induced current can dissipate energy and can oppose the direction of the change of the externally applied field (e.g., given by Lenz's law). The induced current tends to curl away from its initial direction, forming an "eddy current" over the surface of the conductor, such as due to Lorentz forces acting upon electrons moving through the conductor. Because non-ideal conductors have a finite resistivity, the flow of induced current through the conductor can dissipate heat. The induced heat can cause a significant temperature rise in or near the conductor over the duration of the scan. The power dissipated by the eddy current can be proportional to the square of both the peak flux density and the frequency of the excitation.

Generally, induced currents, such as induced by the RF magnetic excitation pulse, can concentrate near the surface of a conductor, a phenomenon that can be referred to as the skin effect. The skin effect can limit both the magnitude and depth of the induced current, thus reducing power dissipation. However, the gradient field can include energy at a much lower frequency than the RF magnetic excitation field, which can more easily penetrate through the housing of the IMD. Unlike the field from the RF excitation pulse, the gradient field can more easily induce bulk eddy currents in one or more conductors within the IMD housing, such as within one or more circuits, capacitors, batteries, or other conductors.

Aside from heating, the EMF can create, among other things, non-physiologic voltages that can cause erroneous sensing of cardiac electrical activity, or the EMF can create a voltage sufficient to depolarize cardiac tissue or render the cardiac tissue refractory, possibly affecting pacing therapy. In an illustrative example, an IMD can be connected to one or more leads, such as one or more subcutaneous or intravascular leads positioned to monitor the patient, or to provide one or more therapies to the patient. In this illustrative example, a surface area of a "circuit" including the lead, the housing of the IMD, and a path through at least partially conductive body tissue between an electrode on the lead and the IMD housing can be more than 300 square centimeters, or more than 0.03 square meters. Thus, using Faraday's law, the EMF developed through the body tissue between the electrode (e.g., a distal tip or ring electrode) of the lead and the housing of the IMD can be more than 3 volts (e.g., more than 0.03 square meters times 100 t/s).

In an MR field, an item, such as an IMD, can be referred to as "MR Safe" if the item poses no known hazard in all MRI environments. In an example, MR Safe items can include non-conducting, non-metallic, non-magnetic items, such as a glass, porcelain, a non-conductive polymer, etc. An item can be referred to as "MR Conditional" in the MR field if the item has been demonstrated to pose no known hazards in a specified MRI environment with specified conditions of use (e.g., static magnetic field strength, spatial gradient, time-varying magnetic fields, RF fields, etc.). In certain examples, MR Conditional items can be labeled with testing results sufficient to characterize item behavior in a specified MRI environment. Testing can include, among other things, magnetically induced displacement or torque, heating, induced current or voltage, or one or more other factors. An item known to pose hazards in all MRI environments, such as a ferromagnetic scissors, can be referred to as "MR Unsafe."

In an example, it can be difficult to sense cardiac events using an IMD in the presence a gradient magnetic field, an RF magnetic excitation pulse, or other components of an MR scan (e.g., an active scan). In certain examples, the MR scan can appear to the IMD as intrinsic activity, or can otherwise interfere with physiological signal detection by the IMD, which can lead to inappropriate shock attempts or incorrect pacing or pacing inhibition.

Discriminating Between Physiologic and MR Signals

The present inventors have recognized, among other things, that a system capable of discriminating physiologic signals from MR signals can be beneficial, as the system would not limit cardiac event detection in the presence of an MRI scan. However, this can be a tough problem to solve because components of the MR scan can introduce signals into the system that interfere with physiologic signal detection. In an example, electromagnetic interference (EMI) from high power RF signals getting past filters at the front end of the PG lead connections can disrupt PG operation. In other examples, time-varying gradient magnetic fields can operate in the sense passband of the IMD and can be detected as physiologic in origin or the gradient fields can distort the physiologic signal such that they may not be reliably detected.

In an example, physiological signals can be discriminated from MR signals using frequency transformation of an input signal. Normal sinus rhythm and ventricular tachycardia (VT) and ventricular fibrillation (VF) arrhythmias can be discriminated in the frequency domain. However, frequency transformation can take time, possibly disrupting bradycardia pacing due to extended transport, communication, or other delays. Further, frequency transformation can be computationally intensive, possibly shortening the service life of the IMD.

Excluding Sensed Signals During MR Scan

The present inventors have recognized, among other things, that cardiac events can be detected during an MR procedure by excluding sensed signals during active portions of an MR scan (e.g., during a time-varying gradient magnetic field, an RF magnetic excitation pulse, or other active portions of an MR scan). In an example, an active period of the MR scan can be sensed (e.g., using a transducer, an inductor, etc.), or an indication of an active period can be received (e.g., received from an external sensor, a seamier, a user, or one or more other machines or automated processes), and sensing by the IMD or other sensor can be excluded during the sensed or received active periods.

FIG. 1 illustrates generally an example of a system 100 including an IMD 105 configured to be implanted in a subject, the IMD 105 including a sensing circuit 106 configured to receive physiologic information (e.g., electrical cardiac information, such as an electrocardiogram (ECG), etc.) from the subject.

In an example, the IMD 105 can be configured to provide a therapy to the subject (e.g., pacing therapy, defibrillation therapy, etc.). The IMD 105 can be configured to receive an indication of proximity to a magnetic field, and can be configured to alter at least one therapy parameter in response to the received indication of proximity to the magnetic field. In an example, the system 100 or the IMD 105 can include a static magnetic field sensor (e.g., a Hall effect sensor, a magnetometer, a reed switch, etc.) configured to detect a static magnetic field. In an example, the indication of proximity of the IMD 105 to the magnetic field can be received using the static magnetic field sensor. In other examples, the IMD 105 can be configured to receive at least one of a user indication of the proximity to the magnetic field, or information from an MRI scanner or other device indicative of proximity to the magnetic field.

In an example, the IMD 105 can be configured to receive an indication of an active MRI scan (e.g., an indication of a time-varying gradient magnetic field, an RF magnetic excitation pulse, EMI, etc.) and to inhibit use of the received physiologic information from the subject during at least a portion of the active MRI scan. In an example, the system 100 or the IMD 105 can include an active magnetic field sensor (e.g., a transducer, an antenna, a coil, etc.) configured to detect a time-varying gradient magnetic field, an RF magnetic excitation pulse, or one or more other components of an active magnetic field. In other examples, the IMD 105 can be configured to receive at least one of a user indication of the active MRI scan, or information from an MRI scanner or other device indicative of an active MRI scan.

In an example, the sensing circuit 106 can be configured to receive the physiologic information during at least a portion of an MRI scan, such as while the IMD 105 is in close proximity to an MRI scanner (e.g., proximate a static magnetic field, such as $B_0$), but not during at least a portion of an active MRI scan (e.g., during a time-varying gradient magnetic field, an RF magnetic excitation pulse, or other active portions of an MRI scan).

In an example, the IMD 105 can be configured to inhibit use of the received physiologic information by inhibiting the sensing circuit 106 from receiving physiologic information from the subject during at least a portion of the active MRI scan. In another example, the sensing circuit 106 can be configured to receive physiologic information during the active MRI scan, but the IMD 105 can be configured to ignore or inhibit use of the received physiologic information during at least a portion of the active MRI scan.

Figure 2:
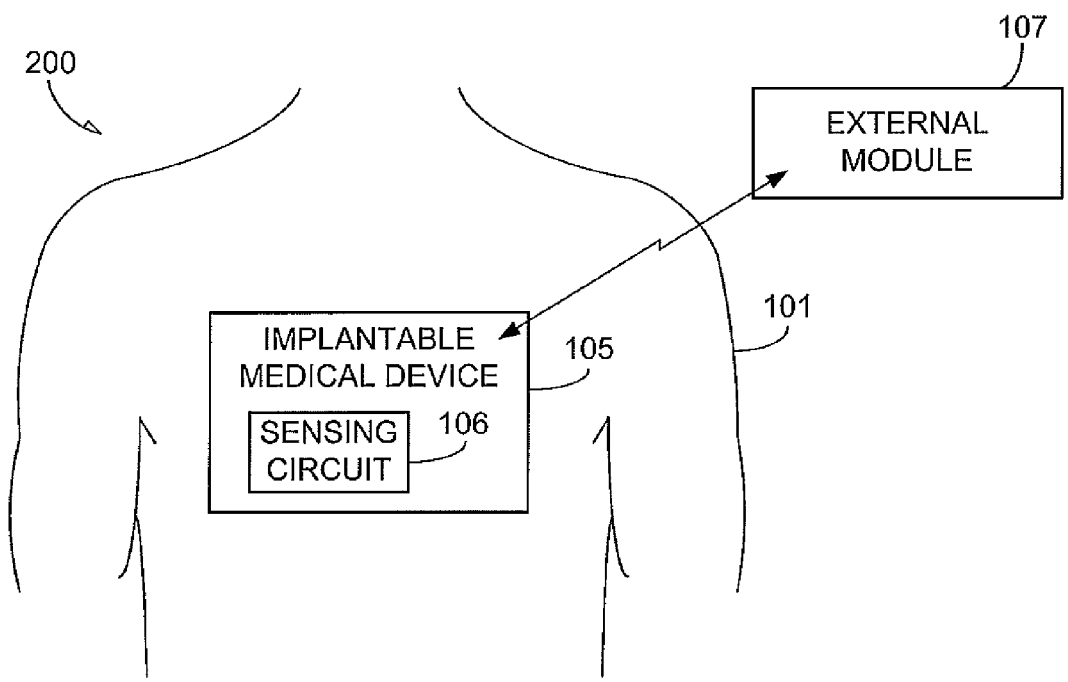
FIG. 2 illustrates generally an example of a system including an IMD and a sensing circuit implanted in a subject.

FIG. 2 illustrates generally an example of a system 200 including an IMD 105 and a sensing circuit 105 implanted in a subject 101, the subject 101 wirelessly coupled to an external module 107 (e.g., a local or remote programmer).

In an example, the IMD 105 can be coupled (e.g., wirelessly, optically, etc.) to one of a local programmer, a remote programmer, or one or more other machines (e.g., an MRI scanner, etc.). In an example, the external module 107 can be configured to receive user information, including MRI instructions.

FIG. 3 illustrates generally an example 300 of a first MRI scan portion 310 of an MRI scan session, including first initial scan slice RF and gradient pulses (herein, "initial pulses") 311, and first variable RF/gradient pulses 312 (herein, "variable pulses"). The dotted line 301 illustrates generally an imaging scan slice start along a timeline 302. FIGS. 4-8 illustrate similar examples.

FIG. 4 illustrates generally an example 400 of first, second, and third scan portions 410, 420, 430 of an MRI scan session, including first, second, and third initial pulses 411, 421, 431 and first, second, and third variable pulses 412, 422, 432.

Generally, an IMD can be configured to inhibit use of physiologic information from a subject (e.g., inhibiting use of received data, inhibiting the receiving of data, etc.) for a period of time following a received indication of an active MRI scan. In certain examples, an initial period can be too short (e.g., an active MRI scan can still be occurring at the end of the initial period). Accordingly, the period following the received indication of the active MRI scan can be adjusted (e.g., increased, increased at a first rate and then decreased at a second rate having a smaller magnitude, etc.) to optimize (e.g., maximize or otherwise specify, etc.) a sense period during the MRI scan or to optimize (e.g., minimize or otherwise specify, etc.) an inhibit period following a received indication of an active MRI scan.

At 413, an indication of an active MRI scan can be received and use of physiologic information from the subject can be inhibited for an initial time period. At 414, the initial time period ends. In this example, because the initial time period ends during the first variable pulse 414, the initial time period can be increased for the next scan portion.

At 423, an indication of an active MRI scan can be received and use of physiologic information from the subject can be inhibited for an increased time period. At 424, the increased time period ends. In this example, because the increased time period ends during the second variable pulse 422, the increased time period can be further increased for the next scan portion.

At 433, an indication of an active MRI scan can be received and use of physiologic information from the subject can be inhibited for an increased time period. At 434, the increased time period ends. In this example, because the increased time period ends outside of the third variable pulse 432, the increased time period can be acceptable, and a sensing period 435 can occur following the increased time period, after 434, and before an indication of an active MRI scan is received, at 443, for a fourth initial pulse 441.

In certain examples, the initial period or the amount of increase can included a predefined value, a user-defined value, or can include information from one or more MRI scanners or one or more previous MRI scan sessions.

FIG. 5 illustrates generally an example 500 of first, second, and third scan portions 510, 520, 530 of an MRI scan session, including first, second, and third initial pulses 511, 521, 531 and first, second, and third variable pulses 512, 522, 532. The example of FIG. 4 illustrated that an acceptable period of time following a received indication of an active MRI scan can be determined. In the example of FIG. 5, an acceptable period of time can be optimized, such as by reducing the time period of FIG. 4 until the time period ends during a variable pulse or other portion of an active MRI scan. In certain examples, the acceptable period of time can be reduced at a smaller rate (e.g., smaller in magnitude) than the rate used to increase the initial time period to the acceptable time period.

At 513, an indication of an active MRI scan can be received and use of physiologic information from a subject can be inhibited for an initial time period (e.g., the acceptable time period of the example of FIG. 4, etc.). At 514, the initial time period ends. In this example, because the initial time period ends outside of the first variable pulse 512, the initial time period can be acceptable, and a sensing period 515 can occur following the initial time period, after 514, and before an indication of an active MRI scan is received, at 523, for the second scan portion 520. In an example, the initial time period can be decreased (e.g., to optimize the sense or inhibit periods, etc.).

At 523, an indication of an active MRI scan can be received and use of physiologic information from the subject can be inhibited for a decreased time period. At 524, the decreased time period ends. In this example, because the decreased time period ends outside of the second variable pulse 522, the decreased time period can be acceptable, and a sensing period 525 can occur following the decreased time period, after 524, and before an indication of an active MRI scan is received, at 533, for the third scan portion 530.

At 533, an indication of an active MRI scan can be received and use of physiologic information from the subject can be inhibited for a decreased time period. At 534, the decreased time period ends. In this example, because the increased time period ends during the third variable pulse 532, the decreased time period cannot be further decreased for a fourth initial pulse 541. Accordingly, in this example, because the decreased time period for the third scan portion 530 fails, the optimal time interval can include the time period for the second scan portion 520, beginning at 523, and ending at 524.

FIG. 6 illustrates generally an example 600 of first, second, and third scan portions 610, 620, 630 of an MRI scan session, including first, second, and third initial pulses 611, 621, 631 and first, second, and third variable pulses 612, 622, 632. The example of FIG. 6 illustrates generally optimal (e.g., maximum or otherwise specified) sense period (e.g., a first, second, or third sense periods 615, 625, 636) utilization following an acceptable and optimized time period.

FIG. 7 illustrates generally an example 700 of a first scan portion 710 including a first initial pulse 711 and a first variable pulse 712. At 713, an indication of an active MRI scan can be received and use of physiologic information from a subject can be inhibited for a time period, beginning at 713, and ending at 714. In this example, because the time period ends outside of the second variable pulse 712, the time period can be acceptable. In certain examples, further optimization can take place (e.g., such as that illustrated in FIG. 5). In this example, a sensing period 715 can occur following the time period, after 714, and before an indication of an active MRI scan is received, at 723, for a second initial pulse 721.

FIG. 8 illustrates generally an example 800 including a more detailed first scan portion 810, including a first initial pulse 811 and a separate first, second, third, and fourth variable pulse portions 812A, 812B, 812C. In an example, the example illustrated in FIG. 8 can include a more detailed or higher resolution scaled version of the example illustrated in FIG. 7.

In certain examples, depending on the time between active MRI scan components during an imaging session, more than one sense period can be located in a single scan portion. In the example of FIG. 8, at 813, an indication of an active MRI scan is received and use of physiological information from a subject can be inhibited for a time period beginning at 813. In this example, a plurality of indications of active MRI scans are received, such as at 813, are received. In an example, each indication of an active MRI scan can include a time before and after where not sense periods should occur.

At 814, the first set of indications of an active MRI scan, such as at 813, end, and a first sense period 815A begins. In the example of FIG. 8, a first, second, third, fourth, and fifth sense periods 815A, 815B, 815C, 815D, 815E exist, whereas in the a similar example of FIG. 7, only a single sense period exists (e.g., the sense period 715 having a similar duration to the sense period 815E). However, although the example of FIG. 8 can provide a longer total sense period, the example of FIG. 8 also can require more processing time, and accordingly, can drastically reduce the life of the IMD.

Other Examples

In an example, an IMD can include one or more implantable leads configured to receive information from a subject or to provide a therapy to the subject. In certain examples, these implantable leads or the IMD can receive energy or interference from an MR field. In an example, one or more templates or representative signals can be created using one or more MR scanners or other MR imaging devices. In an example, one or more of these templates or representative signals can be used (e.g., alone, or in combination with one or more other filters, etc.) to remove unwanted noise from physiologic signals in the presence of an MR field.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, the code may be tangibly stored on one or more volatile or non-volatile tangible computer-readable media during execution or at other times. These computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

The claimed invention is:

1. A system comprising:
an implantable medical device (IMD) configured to be implanted into a subject, the IMD including:
a sensing circuit configured to receive physiologic information from the subject during a portion of a magnetic resonance imaging (MRI) session; and
a static magnetic field sensor configured to detect a static magnetic field;
wherein the IMD is configured to:
identify an indication of an active MRI scan;
identify an indication of proximity to a static magnetic field using information about the detected static magnetic field from the static magnetic field sensor;
determine a time period to inhibit use of physiologic information from the subject following the identified indication of the active MRI scan; and
update at least one subject therapy parameter using the indication of proximity to the static magnetic field;
wherein the IMD is configured to inhibit use of the received physiologic information from the subject for an initial time period following the identified indication of the active MRI scan, to identify an indication of a subsequent active MRI scan following the initial time period, and to adjust the initial time period to determine an optimal time period for a subsequent portion of the MRI session using the indication of the subsequent active MRI scan following the initial time period.

2. The system of claim 1, wherein the IMD is configured to increase the initial time period until the IMD identifies an indication of an absence of an active MRI scan.

3. The system of claim 1, wherein the IMD is configured to decrease the initial time period until an indication of the subsequent active MRI scan is identified.

4. The system of claim 1, wherein the IMD is configured to increase the initial time period until the indication of the subsequent active MRI scan is not identified at the end of the increased initial time period, and then to decrease the initial time period until an indication of a further subsequent active MRI scan is identified at the end of the decreased initial time period.

5. The system of claim 4, wherein the IMD is configured to determine an optimal time period, the optimal time period including the last decreased initial time period prior to the indication of the active MRI scan being identified at the end of the initial time period.

6. The system of claim 1, wherein the IMD is configured to identify an indication of an active MRI scan including at least one of a time-varying gradient magnetic field or an RF magnetic excitation pulse, a user indication of an active MRI scan, or information from an MRI scanner indicative of an active MRI scan.

7. The system of claim 1, including an active magnetic field sensor configured to detect at least one of a time-varying gradient magnetic field or an RF magnetic excitation pulse of an active MRI scan; and
wherein the IMD is configured to identify the indication of the active MRI scan using the active magnetic field sensor.

8. The system of claim 1, wherein the active MRI scan and the subsequent active MRI scan are different portions of the same MRI scan session.

9. A system comprising:
an implantable medical device (IMD) configured to be implanted into a subject, the IMD including:
a sensing circuit configured to receive physiologic information from the subject during a portion of a magnetic resonance imaging (MRI) session; and
wherein the IMD is configured to:
identify an indication of an active MRI scan,
inhibit use of physiologic information from the subject for an initial time period following the identified indication of the active MRI scan; and
identify an indication of a subsequent active MRI scan following the initial time period, the MRI scans including at least one of a time-varying gradient magnetic field or an RF magnetic excitation pulse;
wherein the IMD is configured to increase the initial time period until the IMD identifies an indication of an absence of an active MRI scan after the initial time period and then decrease the initial time period until the IMD identifies an indication of a further subsequent active MRI scan after the initial time period to determine an optimal time period.

10. The system of claim 9,
wherein the optimal time period includes the last decreased initial time period prior to the indication of the active MRI scan being identified after the initial time period.

11. The system of claim 9, wherein the active MRI scan and the subsequent active MRI scan are different portions of the same MRI scan session.

12. A method comprising:
receiving physiologic information from a subject during a portion of a magnetic resonance imaging (MRI) session using a sensing circuit of an implantable medical device (IMD);
identifying an indication of proximity to a magnetic field using information from a static magnetic field sensor;
identifying an indication of an active MRI scan using the IMD;
determining a time period to inhibit the IMD from using the physiologic information from the subject following the identified indication of the active MRI scan; and
inhibiting the IMD from using the physiologic information from the subject during the determined time period;
wherein the determining the time period includes:
inhibiting use of the received physiologic information from the subject for an initial time period following the identified indication of the active MRI scan;
identifying an indication of a subsequent active MRI scan following the initial time period; and
adjusting the initial time period to determine an optimal time period for a subsequent portion of the MRI session using the indication of the subsequent active MRI scan following the initial time period.

13. The method of claim 12, wherein the adjusting the initial time period includes increasing the initial time period until an indication of an MRI scan is not identified.

14. The method of claim 12, wherein the adjusting the initial time period includes decreasing the initial time period until an indication of a further subsequent active MRI scan is identified.

15. The method of claim 12, wherein the adjusting the initial time period includes:
increasing the initial time period at a first rate until an indication of the subsequent active MRI scan is not identified at the end of the increased initial time period, and then decreasing initial time period at a second rate until an indication of a further subsequent active MRI scan is identified at the end of the decreased initial time period, wherein the second rate is larger in magnitude than the first rate.

16. The method of claim 15, including determining an optimal time period, the optimal time period including the last decreased initial time period prior to the indication of the further subsequent active MRI scan identified at the end of the decreased initial time period.

17. The method of claim 12, including identifying at least one of an indication of the active MRI scan including at least one of a time-varying gradient magnetic field or an RF magnetic excitation pulse, a user indication of an active MRI scan, or information from an MRI scan, or information from an MRI scanner indicative of an active MRI scan.

18. The method of claim 12, including detecting at least one of a time-varying gradient magnetic field or an RF magnetic excitation pulse of an active MRI scan using an active magnetic field sensor; and
wherein the identifying the indication of the active MRI scan includes receiving information from the active magnetic field sensor.

* * * * *